US00PP34116P2

(12) United States Plant Patent
Mathey

(10) Patent No.: US PP34,116 P2
(45) Date of Patent: Apr. 12, 2022

(54) ***ARONIA* PLANT NAMED 'SMNAMPEM'**

(50) Latin Name: *Aronia melanocarpa*
Varietal Denomination: SMNAMPEM

(71) Applicant: Megan M. Mathey, Holland, MI (US)

(72) Inventor: Megan M. Mathey, Holland, MI (US)

(73) Assignee: SPRING MEADOW NURSERY INC., Grand Haven, MI (US)

( * ) Notice: Subject to any disclaimer, the term of this patent is extended or adjusted under 35 U.S.C. 154(b) by 0 days.

(21) Appl. No.: 17/492,622

(22) Filed: Oct. 3, 2021

(51) Int. Cl.
*A01H 5/00* (2018.01)
*A01H 6/74* (2018.01)

(52) U.S. Cl.
USPC ..... Plt./156
CPC ..... *A01H 6/74* (2018.05)

(58) Field of Classification Search
USPC ..... Plt./156
CPC ..... A01H 5/00; A01H 5/08
See application file for complete search history.

*Primary Examiner* — Kent L Bell
(74) *Attorney, Agent, or Firm* — C. Anne Whealy

(57) ABSTRACT

A new and distinct cultivar of *Aronia* plant named 'SMNAMPEM', characterized by its relatively compact, upright, outwardly spreading and uniformly rounded plant habit; moderately vigorous growth habit; freely branching habit; medium green-colored leaves that become bright reddish orange during the autumn; upright inflorescences with numerous white-colored flowers; relatively large almost black-colored fruits; and good garden performance.

3 Drawing Sheets

Figure 1:
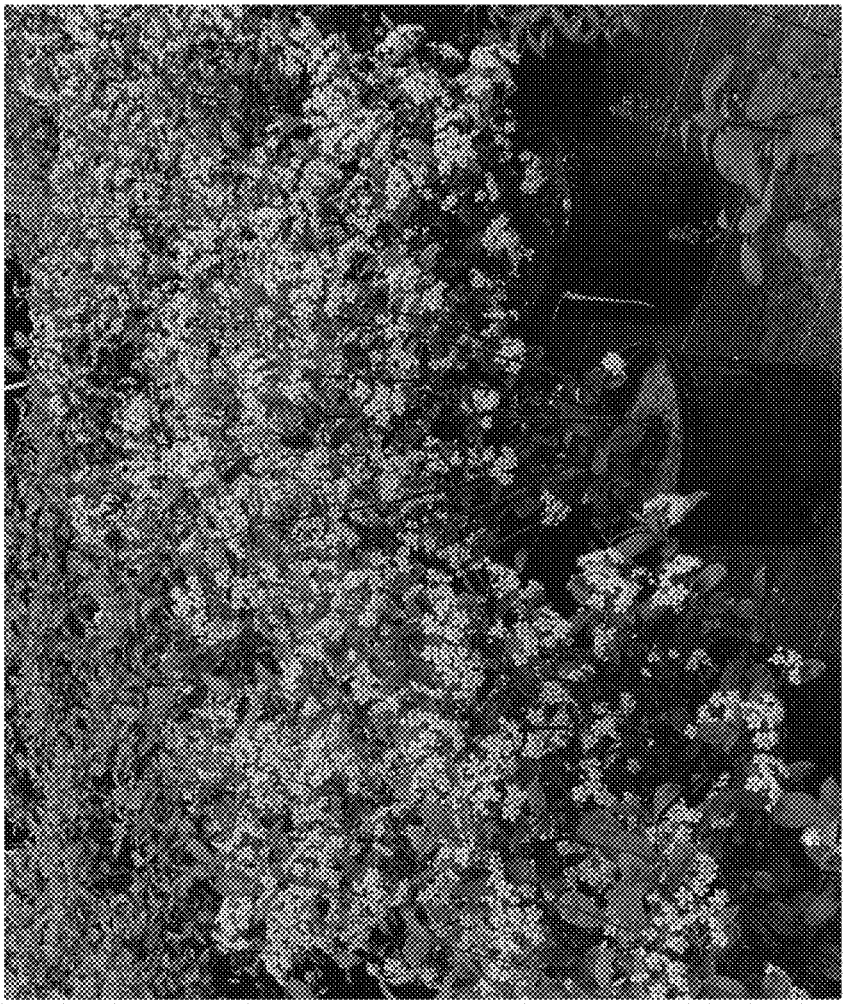

Botanical designation: *Aronia melanocarpa.*
Cultivar denomination: 'SMNAMPEM'.

STATEMENT REGARDING PRIOR DISCLOSURES BY INVENTOR/APPLICANT & ASSIGNEE

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct *Aronia* plant, botanically known as *Aronia melanocarpa*, commonly referred to as Black Chokeberry and hereinafter referred to by the name 'SMNAMPEM'.

The new *Aronia* plant is a product of a controlled breeding program conducted by the Inventor in Grand Haven, Mich. The objective of the breeding program is to create compact and freely flowering *Aronia* plants with attractive autumn leaf color and large decorative fruits.

The new *Aronia* plant originated from an open-pollination in 2014 in Grand Haven, Mich. of *Aronia melanocarpa* 'Professor Ed', not patented, as the female, or seed, parent with an unknown selection of *Aronia malanocarpa* as the male, or pollen, parent. The new *Aronia* plant was discovered and selected by the Inventor in 2017 as a single flowering plant within the progeny of the stated open-pollination in a controlled environment in Grand Haven, Mich.

Asexual reproduction of the new *Aronia* plant by softwood stem cuttings in a controlled environment in Grand Haven, Mich. since 2017 has shown that the unique features of this new *Aronia* plant are stable and reproduced true to type in successive generations of asexual reproduction.

SUMMARY OF THE INVENTION

Plants of the new *Aronia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNAMPEM'. These characteristics in combination distinguish 'SMNAMPEM' as a new and distinct *Aronia* plant:

1. Relatively compact, upright, outwardly spreading and uniformly rounded plant habit.
2. Moderately vigorous growth habit.
3. Freely branching habit.
4. Medium green-colored leaves that become bright reddish orange during the autumn.
5. Upright inflorescences with numerous white-colored flowers.
6. Relatively large almost black-colored fruits.
7. Good garden performance.

Plants of the new *Aronia* can be compared to plants of the female parent, 'Professor Ed'. Plants of the new *Aronia* differ from plants of 'Professor Ed' in the following characteristics:

1. Plants of the new *Aronia* are more freely flowering than plants of 'Professor Ed'.

2. Plants of the new *Aronia* produce more fruits per plant than plants of 'Professor Ed'.
3. Plants of the new *Aronia* produce larger fruits than plants of 'Professor Ed'.

Plants of the new *Aronia* can be compared to plants of the *Aronia melanocarpa* 'UCONNAM165', disclosed in U.S. Plant Pat. No. 28,789. In side-by-side comparisons, plants of the new *Aronia* differ from plants of 'UCONNAM165' in the following characteristics:

1. Plants of the new *Aronia* are slightly taller than plants of 'UCONNAM165'.
2. Plants of the new *Aronia* are more freely branching than plants of 'UCONNAM165'.
3. Plants of the new *Aronia* are more freely flowering than plants of 'UCONNAM165'.

BRIEF DESCRIPTION OF THE PHOTOGRAPHS

The accompanying colored photographs illustrate the overall appearance of the new *Aronia* showing the colors as true as it is reasonably possible to obtain in colored reproductions of this type. Colors in the photographs may differ slightly from the color values cited in the detailed botanical description which accurately describe the colors of the new *Aronia*.

The photograph on the first sheet (FIG. 1) is a side perspective view of typical flowering plants of 'SMNAMPEM' grown in containers.

Figure 2:
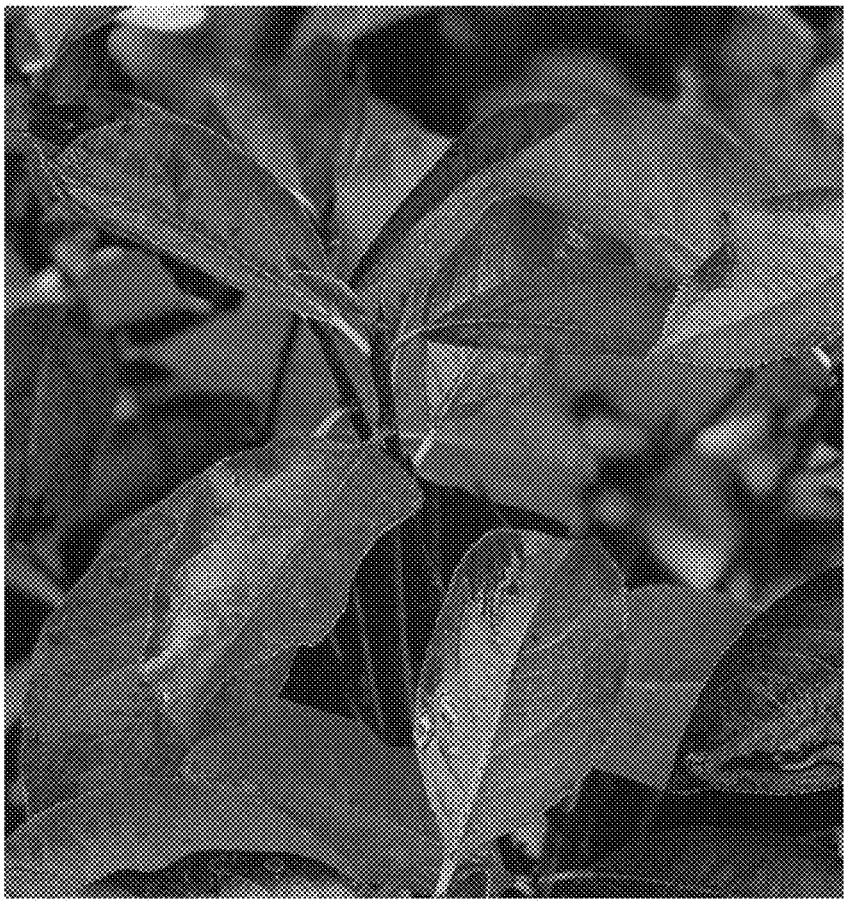

The photograph on the second sheet (FIG. 2) is a close-up view of typical leaves of 'SMNAMPEM' during the autumn.

Figure 3:
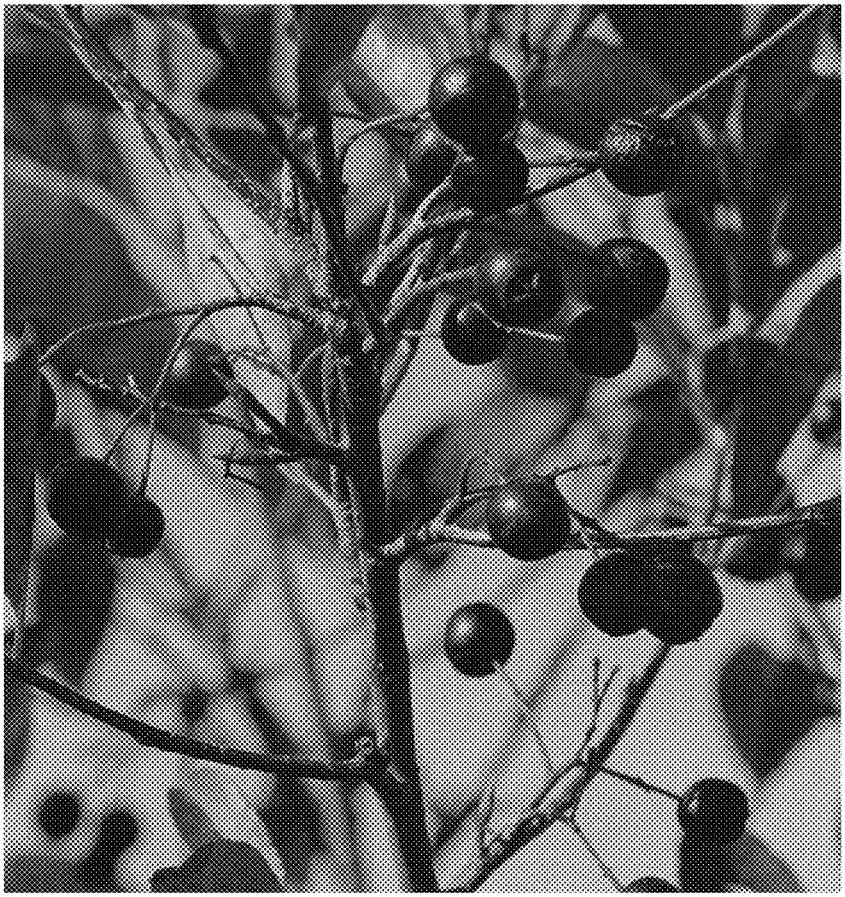

The photograph on the third sheet (FIG. 3) is a close-up view of typical fruits of 'SMNAMPEM'.

DETAILED BOTANICAL DESCRIPTION

The aforementioned photographs and following observations, measurements and values describe plants grown throughout the year in three-gallon containers in a polyethylene-covered greenhouse in Grand Haven, Mich. and under cultural practices typical of commercial *Aronia* production. During the production of the plants, day temperatures ranged from 18° C. to 27° C. and night temperatures ranged from ranged from 5° C. to 10° C. Plants were two years old when the photographs and the description were taken. In the description, color references are made to The Royal Horticultural Society Colour Chart, 2015 Edition, except where general terms of ordinary dictionary significance are used.

Botanical classification: *Aronia melanocarpa* 'SMNAMPEM'.

Parentage:

*Female, or seed, parent.*—*Aronia melanocarpa* 'Professor Ed', not patented.

*Male, or pollen, parent.*—Unknown selection of *Aronia melanocarpa*, not patented.

Propagation:

*Type.*—By softwood stem cuttings.

*Time to initiate roots, summer.*—About three weeks at temperatures about 18° C. to 27° C.

*Time to produce a rooted young plant, summer.*—About eight weeks at temperatures about 18° C. to 27° C.

*Root description.*—Medium in thickness; fibrous; typically white in color, actual color of the roots is dependent on substrate composition, water quality, fertilizer, substrate temperature and physiological age of roots.

*Rooting habit.*—Moderately freely branching; medium density.

Plant description:

*Plant and growth habit.*—Deciduous shrub; relatively compact, upright, outwardly spreading and uniformly rounded plant habit; moderately vigorous growth habit and rapid growth rate.

*Plant height.*—About 56 cm.

*Plant diameter* (*area of spread*).—About 63 cm.

Lateral branch description:

*Branching habit.*—Freely branching habit with about twelve lateral branches developing per plant; pinching enhances lateral branch development.

*Length.*—About 50 cm.

*Diameter.*—About 5 mm.

*Internode length.*—About 4 cm to 6 cm.

*Texture.*—Smooth, glabrous.

*Aspect.*—About 15° to 30° from vertical.

*Strength.*—Strong.

*Color, developing, upper surface.*—Close to 174C.

*Color, developing, lower surface.*—Close to 145A.

*Color, developed, upper and lower surfaces.*—Close to 199B.

*Lenticels.*—Quantity: Moderate to dense. Length: Less than 1 mm. Color: Close to 173C.

Leaf description:

*Arrangement.*—Alternate; single.

*Leaf length.*—About 5.5 cm to 8 cm.

*Leaf width.*—About 3 cm to 5 cm.

*Shape.*—Elliptic.

*Apex.*—Cuspidate.

*Base.*—Attenuate.

*Margin.*—Serrate.

*Texture, upper and lower surfaces.*—Smooth, glabrous; slightly coriaceous.

*Venation pattern.*—Pinnate.

*Color.*—Developing leaves, upper and lower surfaces: Close to 146B. Fully expanded leaves, upper surface: Close to 137A; venation, close to 146C; in the autumn, color becoming closer to between 171A and 173A. Fully expanded leaves, lower surface: Close to 147B; venation, close to 146C; in the autumn, color becoming closer to 165C to 165D.

*Petioles.*—Length: About 7.5 mm. Diameter: About 1.5 mm. Texture, upper surface: Smooth, glabrous. Texture, lower surface: Slightly pubescent. Color, upper and lower surfaces: Close to 146C.

*Stipules.*—Length: About 2 mm. Color: Close to 146C.

Flower description:

*Flower type and flowering habit.*—Single rotate flowers arranged on upright compound corymbs; freely flowering habit with about 40 flowers developing per inflorescence and about 13 to 15 inflorescences developing per plant during the flowering season; flowers face upright to outwardly depending on the position on the inflorescence; flowers not persistent.

*Fragrance.*—Slightly fragrant; floral, pleasant.

*Natural flowering season.*—Plants flower during the spring in Michigan.

*Flower buds.*—Height: About 5 mm. Diameter: About 4 mm. Shape: Spherical. Color: Close to 155B.

*Inflorescence height.*—About 6 cm.

*Inflorescence diameter.*—About 5 cm.

*Flower diameter.*—About 1.5 cm.

*Flower depth.*—About 5 mm.

*Petals*.—Quantity per flower: Typically five in a single whorl. Length: About 6 mm. Width: About 5 mm. Shape: Orbicular. Apex: Rounded. Base: Obtuse with crenate tendencies. Margin: Entire. Texture, upper and lower surfaces: Smooth, glabrous. Color: Developing petals, upper surface: Close to 155B with streaks, close to 70D. Developing petals, lower surface: Close to 155B. Fully developed petals, upper and lower surfaces: Close to 155B.

*Sepals*.—Quantity and arrangement: Typically five sepals per flower arranged in a single whorl, fused at the base. Length: About 2 mm. Diameter: About 1 mm. Shape: Deltoid. Apex: Acute. Base: Truncate. Margin: Entire. Texture, upper surface: Slightly pubescent. Texture, lower surface: Smooth, glabrous. Color, upper and lower surfaces: Close to 145A.

*Peduncles*.—Length: About 4 cm. Diameter: About 1 mm. Strength: Strong. Angle: About 45° to 90° from vertical. Texture: Smooth, glabrous. Color: Close to 145A.

*Pedicels*.—Length: About 1 cm to 2 cm. Diameter: About 1 mm. Strength: Strong. Angle: About 45° to 90° from the peduncle axis. Texture: Smooth, glabrous. Color: Close to 145A.

*Reproductive organs*.—Stamens: Quantity per flower: Typically 18 to 20. Filament length: About 2 mm. Filament color: Close to 155C. Anther length: About 1 mm. Anther color: Close to 63A. Pollen amount: If present, scarce. Pistils: Quantity per flower: Five. Pistil length: About 2 mm. Style length: About 2 mm. Style color: Close to 145C. Stigma shape: Globular. Stigma color: Close to 145C. Ovary color: Close to 145C. Fruits: Quantity per lateral branch: About 10 to 20. Length: About 1.5 cm. Diameter: About 1.5 cm. Shape: Spherical. Texture: Smooth, glabrous. Color: Almost black, close to 203B.

Garden performance: Plants of the new *Aronia* have been observed to have good garden performance.

Pathogen & pest resistance: To date, plants of the new *Aronia* have not been shown to be resistant to pathogens and pests common to *Aronia* plants.

It is claimed:

1. A new and distinct *Aronia* plant named 'SMNAMPEM' as illustrated and described.

* * * * *